United States Patent [19]
Sherman

[11] Patent Number: 6,163,719
[45] Date of Patent: Dec. 19, 2000

[54] BIOLOGICAL MEMBRANE VOLTAGE ESTIMATOR

[76] Inventor: Adam Jacob Sherman, 5205 Durocher Ave, Apt 19, Montreal, Quebec, Canada, H2V 3X9

[21] Appl. No.: 09/149,402

[22] Filed: Sep. 8, 1998

Related U.S. Application Data

[60] Provisional application No. 60/058,532, Sep. 9, 1997.

[51] Int. Cl.[7] ...................................................... A61B 5/05
[52] U.S. Cl. ........................... 600/547; 600/372; 128/897
[58] Field of Search ................... 600/547, 372, 600/373, 382; 128/897, 898

[56] References Cited

U.S. PATENT DOCUMENTS

| | | | |
|---|---|---|---|
| 3,971,366 | 7/1976 | Motoyama | 600/547 |
| 4,055,799 | 10/1977 | Coster et al. | 324/71 R |
| 4,441,507 | 4/1984 | Steffin | 128/734 |
| 4,452,249 | 6/1984 | Sachs et al. | 600/396 |
| 4,510,442 | 4/1985 | Neher | 324/99 R |
| 4,912,060 | 3/1990 | Fein | 600/547 |

OTHER PUBLICATIONS

Sigworth, F.J. 1983. Electronic Design of the Patch Clamp. In Single–Channel Recording. B. Sakmann, and E. Neher, editors. Plenum Press, New York. pp. 3–35.

Guld, C. 1962. Cathode follower and negative capacitance as high input impedance circuits. *Proc. IRE.* 50:1912–1927.

Moore, J. W., M Hines, and E. M. Harris. 1984. Compensation for resistance in series with excitable membranes. *Biophys. J.* 46:507–514.

Strickholm, A. 1995. A single electrode voltage, current and patch–clamp amplifier with complete stable series resistance compensation. *J. Neurosci. Methods.* 61:53–66.

Strickholm, A. 1995. A supercharger for single electrode voltage and current clamping. *J. Neurosci. Methods.* 61:47–52.

Brennecke, R. and B. Lindemann. 1972. Theory of a membrane voltage clamp with discontinuous feedback through a pulsed current clamp. *Rev. Sci. Instrum.* 45:184–188.

Wilson, W.A, and M. M. Goldner. 1975. Voltage clamping with a single microelectrode. *J. Neurobiol.* 6:411–22.

Finkel, A. S., and S. J. Redman. 1984. Theory and operation of a single microelectrode voltage clamp. *J. Neurosci. Methods.* 11:101–127.

Sherman, A.J. , A. Shrier, and E. Cooper. 1997. A novel technique for series resistance compensation. *Soc. Neurosci. Abstr.,* 23:1473.

*Primary Examiner*—Cary O'Connor
*Assistant Examiner*—Charles Marmor, II

[57] ABSTRACT

A method and apparatus for estimating the membrane voltage of a cell that is independent of cell conductance. This estimated voltage is used to implement stable, complete (100%) series resistance compensation for a single electrode voltage clamp amplifier, enabling the recording of rapid ionic currents in single, excitable cells.

20 Claims, 5 Drawing Sheets

BIOLOGICAL MEMBRANE VOLTAGE ESTIMATOR

CROSS-REFERENCES TO RELATED APPLICATIONS

This applications claims the benefit of Provisional Patent Application Ser. No. 60/058,532 filed Sep. 9, 1997.

BACKGROUND OF INVENTION

1. Field of the Invention

This invention relates to the study of ionic current due to membrane conductance changes in single cells. Much of the electrophysiology of cells—such as the generation of the action potential—is related to the flow of ionic current across the cell membrane in response to complex membrane conductance changes. To understand the electrophysiology of such cells, it is necessary measure this ionic current and characterize the membrane conductance changes.

2. Description of the Prior Art
The Voltage Clamp Amplifier

Figure 1A:
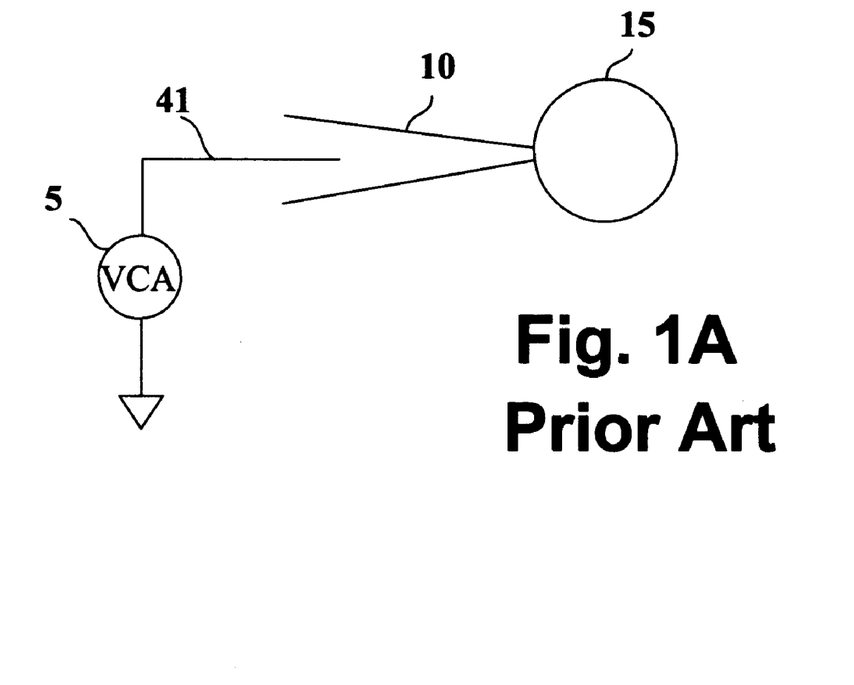
FIG. 1A and 1B show a voltage clamp amplifier with a recording pipette and a cell, along with an equivalent circuit (Prior Art)

An apparatus know as a voltage clamp amplifier (VCA), in conjunction with a glass pipette electrode, is used to measure ionic current and conductance in single cells, as shown in FIG. 1A.

Figure 1B:
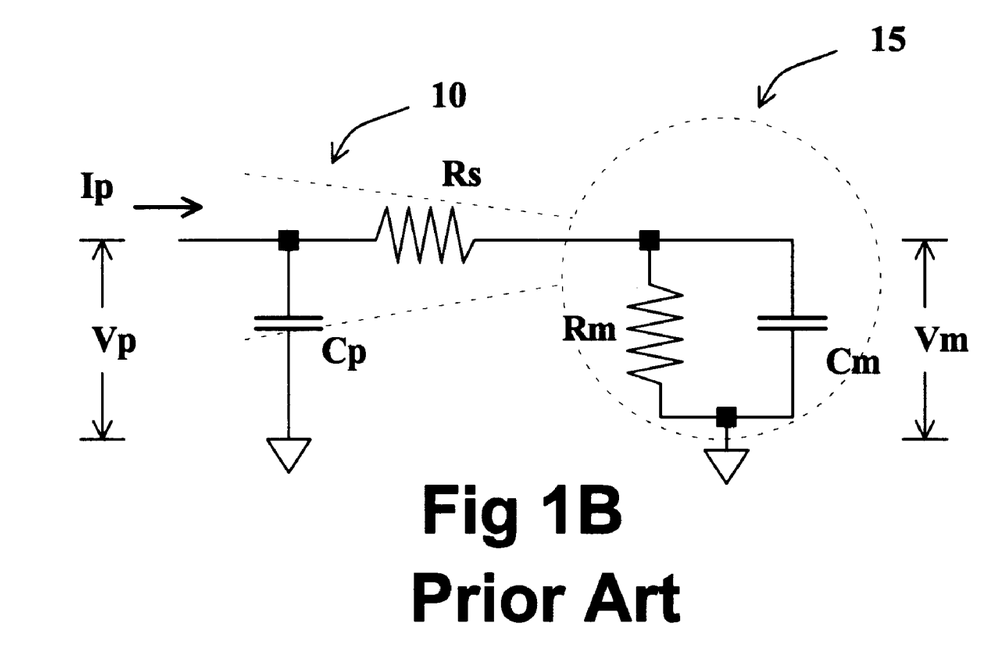

Referring to FIG. 1A, a VCA 5 generates a command voltage Vc 41, and is connected to a cellular microelectrode, patch electrode or pipette electrode 10, the fabrication of which is well known in the art. Pipette 10 is in electrical contact with a cell 15. FIG. 1B shows an equivalent circuit of pipette 10 and cell 15. As shown, pipette 10 has a pipette series resistance Rs, a pipette shunt capacitance Cp, a pipette voltage Vp, and a pipette current Ip. Thus pipette 10 is modeled by a single RC section formed by Rs and Cp. Cell 15 has a membrane resistance Rm, a membrane capacitance Cm, and a membrane voltage Vm.

The VCA acts as a low impedance voltage source, setting the pipette voltage Vp equal to the command voltage Vc 41. If Rs and Cp are small enough to be ignored, the cell membrane voltage Vm≈Vp and Vc 41 is imposed across the cell membrane. Vm is then said to be "clamped" to Vc. Under these conditions, measuring the pipette current Ip provides a direct measure of the cellular ionic current. The cellular ionic conductance G can then be computed as:

$$G = \frac{I_p}{V_p}$$

The Effects of Series Resistance (Rs)

In practice, the main difficulty with this arrangement is that the large pipette series resistance Rs limits the voltage clamping bandwidth. The time constant that determines voltage clamping bandwidth is given by:

$$\tau_{vclamp} = R_s C_m$$

A typical Rs, Cm combination of 5 Meg and 50 pF gives a time constant of 250 us, or a bandwidth of 637 Hz. While this is sufficient bandwidth to record slow ionic currents, rapid ionic currents—such as $Na^+$ current that underlies the action potential in cardiac or neuronal cells—require a voltage clamping bandwidth of ~10 kHz to be resolved. Therefore, in order to voltage clamp rapid ionic currents in single cells, it is necessary to compensate for the bandwidth-lowering effects of series resistance.

Rs Compensation

Three principal methods are in use to compensate for series resistance effects using a single electrode VCA: conventional Rs compensation, steady state Rs compensation, and compensation using discontinuous or pulsed feedback. Each method is only partially effective, so that voltage clamping rapid ionic current using these methods—especially in large cells where the membrane capacitance Cm is large—is extremely difficult.

Conventional Rs Compensation

Figure 2:
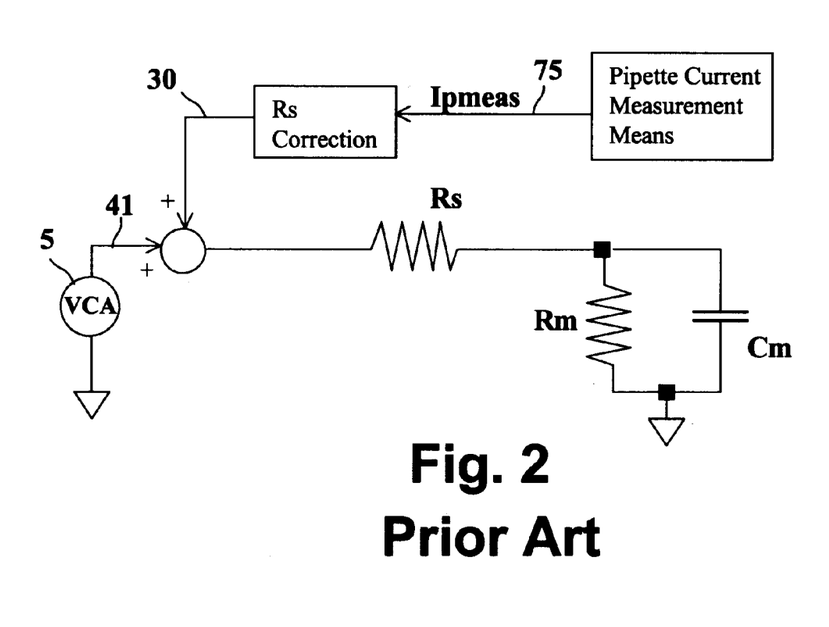
FIG. 2 shows conventional Rs compensation (Prior art)

Conventional Rs compensation is widely used to increase the recording bandwidth of the single electrode VCA (see *Electronic Design of the Patch Clamp* by F. J. Sigworth, 1983, found in *Single-Channel Recording*, edited by B. Sakmann and E. Neher, p. 29–32.). As shown in FIG. 2, conventional Rs compensations uses a feedback circuit to add an Rs correction signal Rscorr 30 to the command voltage Vc. Rscorr 30 is computed as a scaled value of the measured pipette current Ipmeas 75, where Ipmeas 75 comes from pipette current measurement means 74. Rscorr 30 is given by:

$$Rscorr = I_{pmeas} R_s \alpha$$

where α is a scaling constant ranging from 0 (no Rs compensation) to 1 (100% Rs compensation). Ideally, when α→1 the membrane voltage Vm follows the command voltage Vc exactly, independently of Rs. In practice, conventional Rs compensation is unstable at high compensation settings. Sigworth's analysis traces the main cause of this instability to stray capacitance effects of the pipette electrode: conventional Rs compensation as shown in FIG. 2 assumes pipette 5 behaves like a pure resistance Rs, whereas a real pipette electrode has stray shunt capacitance Cp (as shown previously in FIG. 1B). Pipette current shunted through this stray capacitance introduces an erroneous correction signal that destabilizes the Rs compensation feedback loop. To improve stability it is necessary to neutralize this stray pipette capacitance electronically using a positive feedback network. This capacitance neutralization circuitry is itself prone to instability (see Guld, C. 1962. Cathode follower and negative capacitance as high input impedance circuits, Proc. IRE. 50:1912–1927). Consequently, even when using maximum capacitance neutralization α is limited to ~0.8, corresponding to 80% series resistance compensation. This is usually insufficient to voltage clamp fast ionic current. In addition, slight shifts in Rs or Cp—as happens when the pipette immersion depth changes—easily drives conventional Rs compensation circuitry from a marginally stable state into oscillation, killing the cell under study.

Steady State Rs Compensation

Moore et. al. (Moore, J. W., M Hines, and E. M. Harris. 1984. Compensation for resistance in series with excitable membranes. *Biophys. J.* 46:507–514) and Strickholm (Strickholm, A. 1995. A single electrode voltage, current and patch-clamp amplifier with complete stable series resistance compensation. *J Neurosci. Methods*. 61:53–66.) each describe similar modifications to conventional Rs compensation that feed back a scaled value of the steady state pipette current as opposed the total pipette current. In steady state Rs compensation, Rscorr 30 is given by:

$$Rscorr = I_{steady-state} R_s \alpha$$

where $I_{steady-state}$ is computed using an electronic bridge circuit that subtracts the membrane capacitive current from the measured pipette current Ipmeas 75. Steady state Rs compensation is not destabilized by stray pipette capacitance—as is the case with conventional Rs compensation—and 100% compensation values can be used. By subtracting the membrane capacitive current, there is effectively no Rs compensation when the command potential Vc changes. Consequently, to increase the rate of membrane charging when Vc is changed, Strickholm outlines the use of a supercharging potential that is added to Vc. ( see Strickholm, A. 1995. A supercharger for single electrode voltage and current clamping. *J Neurosci. Methods.* 61:47–52).

Limitations of Steady State Rs Compensation

Figure 3:
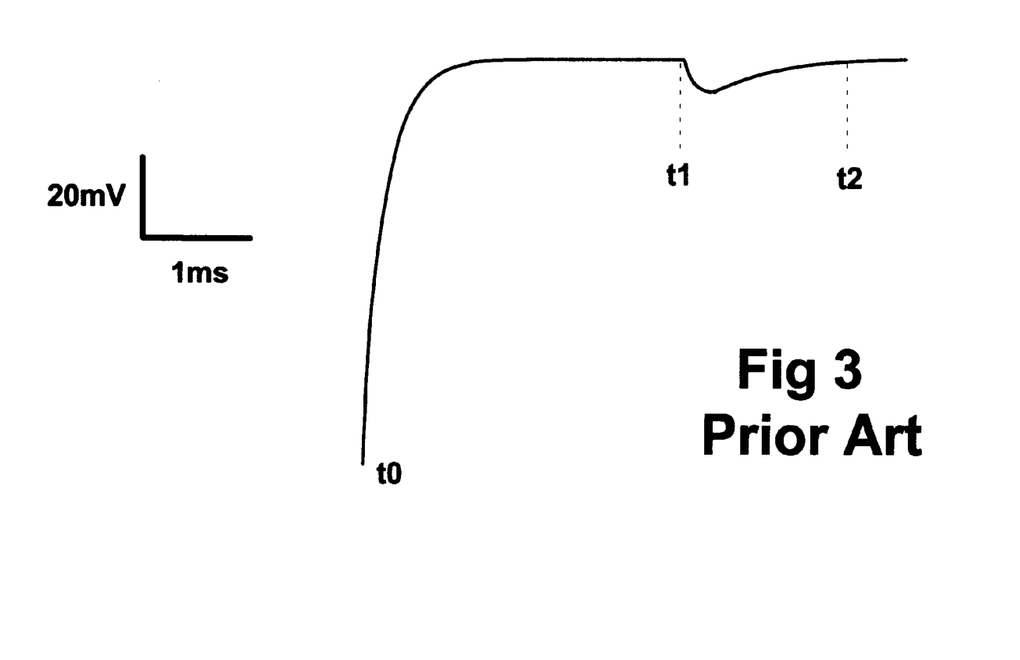
FIG. 3 shows the effects of large cell conductance changes using steady state Rs compensation (Prior art)

A serious limitation with steady state Rs compensation occurs when the system is used with a single electrode VCA to voltage clamp large, rapidly activating ionic currents such as $Na^+$ current in single cells. This limitation is due to the fact that the electronic bridge assumes a fixed value for the membrane resistance Rm in order to compute and subtract off the membrane capacitive current. When large ionic currents are voltage clamped, Rm can change by factors of 100 or more and unbalance the electronic bridge. When this happens the voltage clamp recovery time can be >1 ms, which is too slow to maintain voltage clamp control of rapid ionic currents. This situation is shown in FIG. 3. FIG. 3 plots the membrane voltage Vm using steady state Rs compensation. Initially Rs=5 Meg, Rm=100 Meg, and Cm=50 pF—typical values for a pipette electrode and cell—and the electronic bridge is balanced for these values. At t0 the command voltage undergoes a stepwise transition from 0 to 100 mV. After ~1 ms the membrane voltage charges to the command voltage of 100 mV. At t1 Rm makes a stepwise transition from 100 Meg to 20 Meg, simulating a rapid, large ionic conductance change. As shown, the membrane voltage Vm escapes from the clamping voltage of 100 mV at t1, and takes until t2 before Vm is again clamped at 100 mV. It should be noted that using the supercharging procedure described by Strickholm will increase the initial rate of membrane charging when Vc is changed at t0, but will not affect in any way the slow voltage clamp recovery time exhibited when Rm changes at t1.

Discontinuous Feedback Amplifiers

Another approach to combat series resistance effects is originally described by Brennecke et. al. (Brennecke, R. and B. Lindemann. 1972. Theory of a membrane voltage clamp with discontinuous feedback through a pulse current clamp. *Rev. Sci. Instrum.* 45:184–188) and implemented by Wilson et. al. (Wilson, W. A, Goldner 1975. Voltage clamping with a single microelectrode. *J Neurobiol.* 6:411–22). Variously called switch-clamp, pulsed current clamp or discontinuous feedback voltage clamp amplifiers, these designs operate on the principle of repetitively cycling between current passing and voltage measuring modes. During voltage measuring mode, the membrane voltage is measured and stored while no current is passed down the electrode. During current passing mode, the stored membrane voltage is compared with the command voltage and used to determine a current injection pulse. This current injection pulse acts as negative feedback to keep the membrane voltage clamped at the command voltage Vc. Since the membrane voltage is measured while no current is being passed down the electrode, there is no voltage drop across Rs, and hence the speed of the clamp becomes independent of Rs. The attainable bandwidth is limited by the maximum switching rate used. Finkel et. al. (Finkel, A. S. and S. J. Redman. 1984. Theory and operation of a single microelectrode voltage clamp. *J. Neurosci. Methods.* 11:101–127) show that the maximum stable switching rate is limited by the stray pipette capacitance Cp. Consequently, in order to increase the switching rate, it is necessary to neutralize the pipette capacitance electronically, as with conventional Rs compensation. This capacitance neutralization compromises the stability of the voltage clamp. The attainable voltage clamp bandwidth using discontinuous feedback is generally insufficient to resolve rapid $Na^+$ currents.

Modified Swtich-Clamp Amplifiers

Steffin obtained U.S. Pat. No. 4,441,507 (1984) by applying modifications to switch clamp designs to improve bandwidth. His patent outlines a high frequency equalization network on the input stage, as well as low frequency and transient compensation networks. His switch clamp also employs electronic capacitance neutralization circuits as with existing designs. Consequently, obtaining rapid switching rates is dependent on finely tuning capacitance neutralization circuitry, as well as tuning the aforementioned equalization and compensation networks. This makes for an unstable voltage clamp that cannot tolerate parameter changes. Slight changes in pipette stray capacitance will lead to unstable operation, as with conventional Rs compensation.

The Twin Electrode Voltage Clamp

Figure 4:
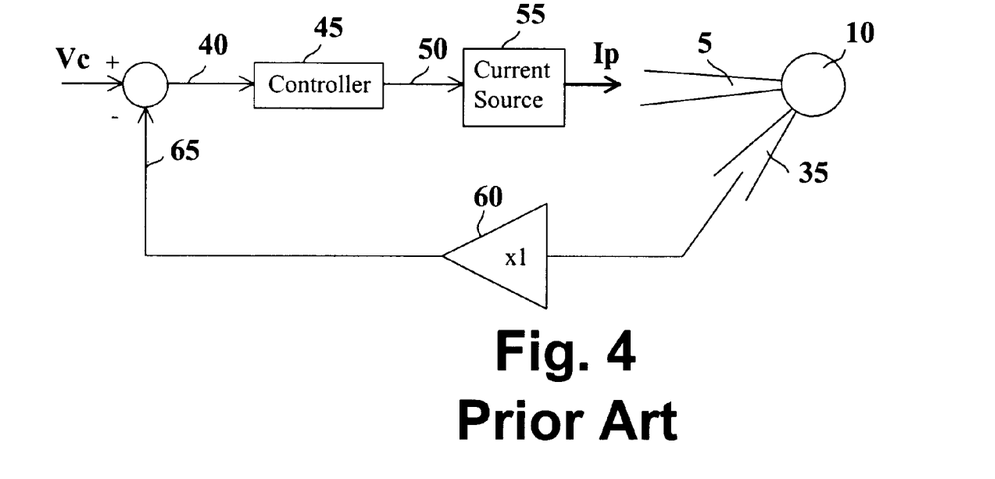
FIG. 4. shows a twin electrode voltage clamp (Prior Art)

A very successful approach to combat series resistance effects is based on using two pipette electrodes instead of one. A twin electrode voltage clamp uses one electrode to measure Vm; the other electrode is used to pass current to clamp the membrane voltage at Vc in a negative feedback loop. Referring to FIG. 4, command voltage 41 is compared to a feedback signal 65. Feedback signal 65 is generated by buffer amplifier 60, which buffers the membrane voltage Vm measured by pipette 35. The result of this voltage comparison forms an error voltage signal 40. The error signal 40 is subject to a feedback controller 45 and a controlled current source 55, the fabrication of which are well known in the art. Controller 45 takes as input error voltage signal 40 and outputs control voltage 50. Current source 55 takes as input control voltage 50 and outputs the pipette current Ip, where Ip is made proportional to the input control voltage 50 by the action of current source 55. The output of current source 55 into pipette 5 and cell 10 acts as negative feedback to clamp the cell membrane potential Vm to the command potential Vc.

With the twin electrode configuration, the series resistance Rs is contained within the feedback loop and hence does not limit the voltage clamping bandwidth.

While the twin electrode configuration creates a wide bandwidth voltage clamp, it is generally unsuitable for use with single cells, owing to the difficulty of impaling two electrodes in single cell. Consequently, to voltage clamp rapid ionic current in single cells requires using a single electrode VCA and compensating for series resistance Rs in some manner.

In summary, the methods of series resistance compensation for a single electrode VCA hithertofore in use all suffer from a number of disadvantages:

a. As they increase bandwidth, there is a corresponding decrease in stability. This makes them extremely difficult to use.

b. Most require the careful use of pipette capacitance neutralization, which further reduces stability.

c. Stable variants assume a fixed membrane conductance, making them too slow to resolve rapid ionic currents.

OBJECTS AND ADVANTAGES

Accordingly, several objects and advantages of the present invention are:

a. to provide full, stable series resistance compensation for a single electrode voltage clamp without the need to null stray capacitance electronically;

b. to provide series resistance compensation for a single electrode voltage clamp that is independent of cell conductance changes, so that large, fast ionic currents can be voltage clamped; and c. to provide series resistance compensation for a single electrode voltage clamp that has wide stability margins, ensuring stable operation even as parameters change during an experiment.

Further objects and advantages of my invention will become apparent from a consideration of the ensuing description and drawings.

DRAWING FIGURES

In the drawings, closely related figures have the same number but different alphabetic suffixes.

SUMMARY OF INVENTION

In accordance with the invention, a means is provided to estimate a cell membrane voltage using a single pipette electrode that is independent of cell conductance changes, and in absence of pipette capacitance neutralization. This estimated membrane voltage is then used in place of a traditional second measuring electrode within a feedback loop, thereby implementing a single electrode voltage clamp with stable, complete (100%) series resistance compensation.

DESCRIPTION OF PREFERRED EMBODIMENTS

Figure 5:
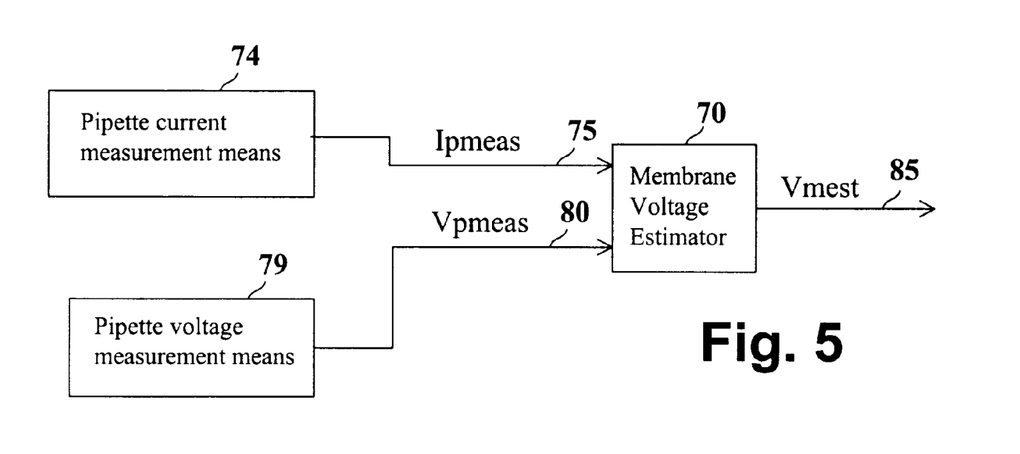
FIG. 5. shows a block diagram of the membrane voltage estimator

Referring to FIG. 5, the invention provides a membrane voltage estimator 70, which generates a computed membrane voltage Vmest 85 which represents the true membrane voltage Vm. Estimator 70 function is independent of cell resistance Rm or cell capacitance Cm, and does not require neutralizing the pipette capacitance Cp electronically. How estimator 70 is used to implement series resistance compensation in a single electrode voltage clamp is shown subsequently in FIG. 8.

As shown in FIG. 5, estimator 70 takes as input Ipmeas 75 and Vpmeas 80, where Ipmeas 75 is a measured signal representing the true pipette current pipette current Ip, and Vpmeas 80 is a measured signal representing the true pipette voltage Vp. Ipmeas 75 is generated by pipette current measurement means 74, and Vpmeas 80 is generated by pipette voltage measurement means 79. The fabrication of measurement means 74 and 79 are well known in the art. Estimator 70 outputs a voltage Vmest 85, which is a computed or estimated value of the true cell membrane voltage Vm.

Estimator 70 performs the following computation to compute Vmest 85:

$$V_{mest} = \underbrace{\tau_p \frac{dV_{pmeas}}{dt}}_{E1.1} + \underbrace{V_{pmeas}}_{E1.2} - \underbrace{I_{pmeas} R_s}_{E1.3} \tag{E1}$$

where $\tau_p$=Rs Cp=pipette time constant.

Note that equation E1 gives Vmest independently of the cell resistance Rm or cell capacitance Cm.

Figure 6A:
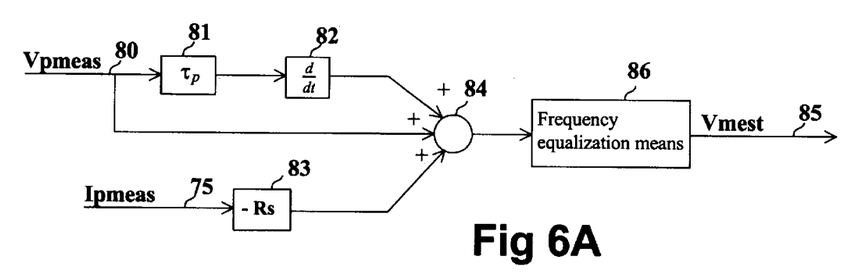
FIG. 6A and 6B show an embodiment of the membrane voltage estimator
Figure 6B:
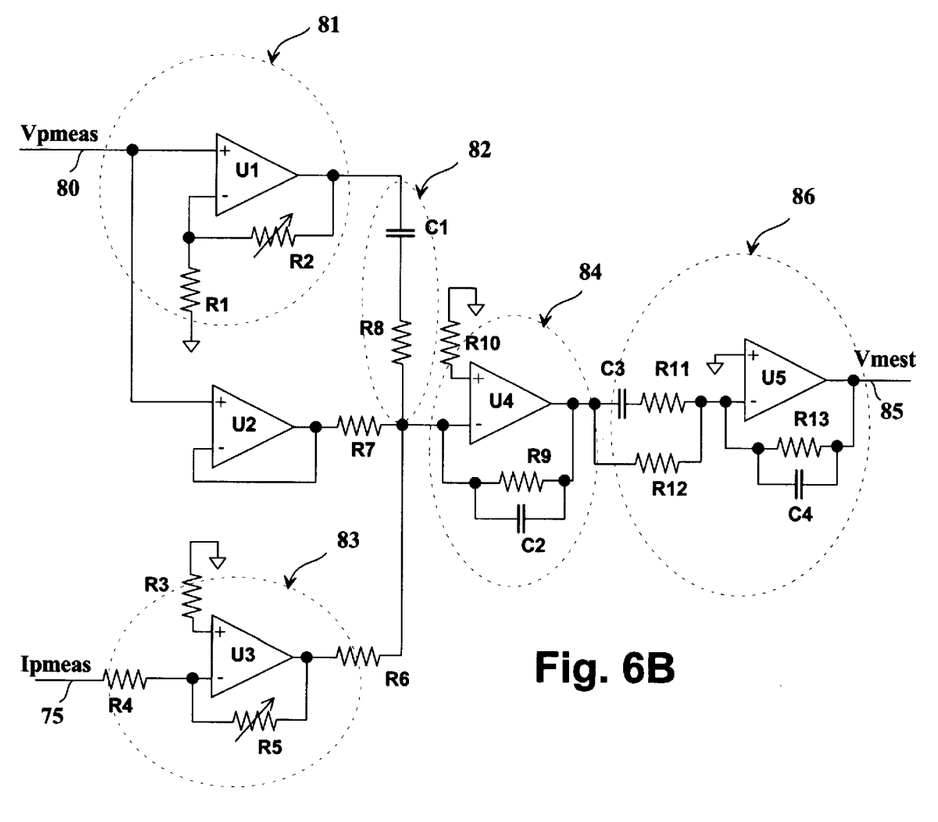

FIG. 6A and 6B outline one embodiment of estimator 70. In the following description of FIGS. 6A and 6B, E1.1 through E1.3 refer to the three bracketed terms of equation E1, shown above.

The embodiment in FIG. 6A is composed of a voltage scaling means 81, a differentiating means 82, a current scaling means 83, a summing means 84, and a frequency equalization means 86 to implement equation E1.

FIG. 6B expands on the block diagram description of 6A. Referring to FIG. 6B, E1.1 is computed by the signal path Vpmeas 80, through U1 configured as a non-inverting amplifier, through capacitor C1 and resistor R8, into the summing junction of U4. The variable gain of non-inverting amplifier U1 is set by potentiometer R2, which introduces the scaling factor $\tau_p$ in E1.1.

E1.2 is computed by the signal path of Vpmeas 80, through U2 configured as a unity gain buffer, through resistor R7, into the virtual ground of U4. The unity gain buffer U2 serves to introduce similar phase shift characteristics to amplifiers U1 and U3 in this signal path.

E1.3 is computed by the signal path of Ipmeas 75, through U3 configured as an inverting amplifier, through resistor R6, into the virtual ground of U4. The variable gain of inverting amplifier U3 is set by potentiometer R5, which introduces the scaling factor Rs in E1.3.

The virtual ground of U4 creates a summing node, summing the terms E1.1, E1.2, and E1.3 of equation E1. The limited gain-bandwidth product of U4 introduces resonance peaks at high frequencies due to the derivative computation of term E1.1. The resonance peaks are minimized by lowering the bandwidth of U4 with resistor R9 in parallel with capacitor C2. R9 and C2 should be chosen to lower the closed-loop output bandwidth of U4 to approximately 1 kHz. The resonance peaks are also diminished by selecting U4 so as to have a high open-loop gain-baindwidth product.

To increase the overall bandwidth of estimator 70, the network formed by capacitor C3, resistor R11 and resistor R12 into the virtual ground of U5 acts as a frequency equalizer, canceling the pole formed by resistor R9 in parallel with capacitor C2. The final bandwidth of estimator 20 is set by resistor R13 in parallel with capacitor C4. Vmest 85 is taken from the output terminal of U5.

Figure 7A:
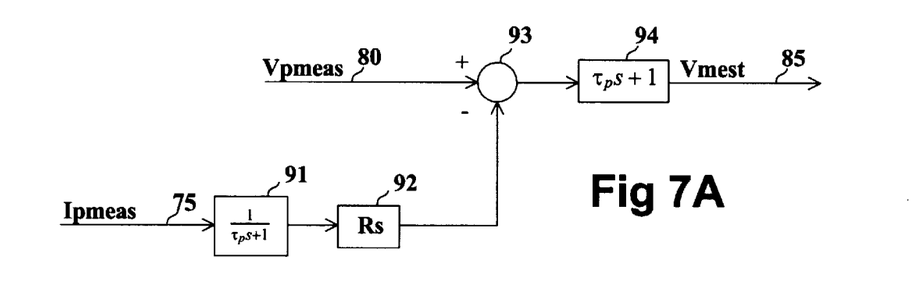
FIG. 7A and 7B show another embodiment of the membrane voltage estimator
Figure 7B:
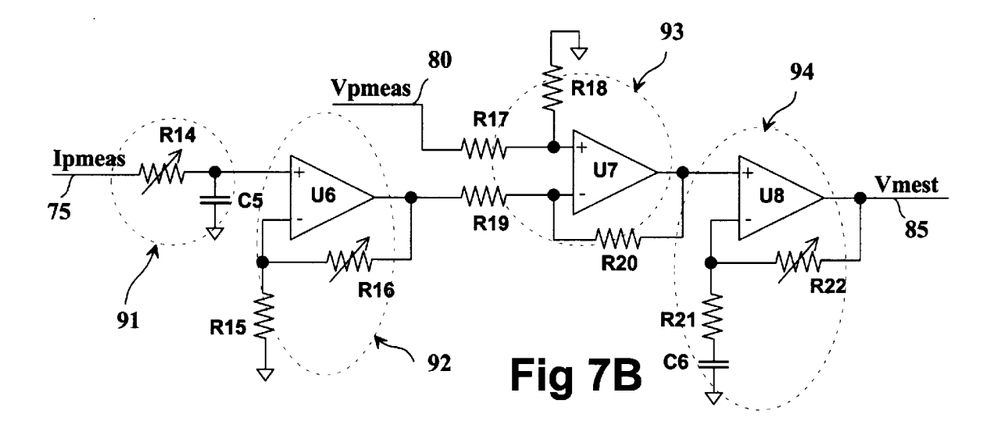

FIG. 7A and 7B outline another embodiment of estimator 70. To understand FIG. 7A and 7B, it is helpful to take the Laplace transform of both sides of equation E1 and rearrange terms, giving:

$$V_{mest}(s) = \left[ \underbrace{V_{pmeas}(s)}_{E2.1} - \underbrace{\frac{I_{pmeas}(s) R_s}{\tau_p s + 1}}_{E2.2} \right] \underbrace{(\tau_p s + 1)}_{E2.3} \tag{E2}$$

Equation E2 is mathematically equivalent to equation E1. In the following description of FIG. 7A and 7B, E2.1 through E2.3 refer to the three bracketed terms of equation E2, shown above.

The embodiment in FIG. 7A is composed of a lowpass filter means 91, a scaling means 92, a differencing means 93, and a frequency equalization means 94 to implement equation E2.

FIG. 7B expands on the block diagram description of 7A. Referring to FIG. 7B, E2.1 is computed by the signal path Vpmeas 80, through resistor R17, into U7 which is configured as a differential amplifier. The differential amplifier U7 subtracts E2.2 from E2.1

E2.2 is computed by the signal path Ipmeas 75, filtered by the lowpass 91 filter formed by potentiometer R14 and capacitor CS, into U6 configured as a non-inverting amplifier, and into U7 configured as a differential amplifier. The potentiometer R14 is set so that the time constant formed by R14 and CS is equal to the pipette time constant $\tau_p$=Rs Cp. The variable gain of non-inverting amplifier U6 is set by potentiometer R16, which introduces the scaling factor Rs in E2.2.

E2.3 is introduced by feeding the output of U7 into the non-inverting amplifier formed by U8, resistor R21, potentiometer R22, and capacitor C6. To introduce the time constant $\tau_p$ in E2.3, the potentiometer R22 is set so that:

$$(R21+R22)C6=\tau_p \tag{E3}$$

Vmest 85 is taken from the output terminal of U8, the overall bandwidth of Vmest 85 being set by the time constant formed by R21 and C6.

If the pipette time constant $\tau_p$ is minimized, frequency equalization means 94 can be omitted, in which case Vmest 85 is taken from the output terminal of U7 instead of the output terminal of U8. To minimize $\tau_p$, the pipette capacitance Cp can be mininized by using low immersion depths, or by coating pipette 10 with a hydrophobic substance, as is well known in the art.

In the embodiment in FIG. 6B, it is important to match the phase characteristics of the signal paths computing E1.1, E1.2, and E1.3 for accurate estimator function at high frequencies. Similarly, in the embodiment of FIG. 7B, it is important to match the phase characteristics of the signal paths computing E2.1 and E2.2. This phase matching criteria can be met in embodiment in FIG. 7 with less expensive components than in FIG. 6, because forming the derivative in term E1.1 requires U4 to have a high gain-bandwidth product, while this is not the case for the embodiment in FIG. 7B. Nonetheless, both embodiments work well.

OPERATION OF INVENTION

The membrane voltage estimator 70 is used to implement series resistance compensation for a single electrode voltage clamp by using any one of several two electrode voltage clamp configurations known in the art, but replacing the second voltage measuring electrode with the membrane voltage estimator 70. The estimator thus functions as a "virtual" electrode in place of the actual measuring electrode.

Figure 8:
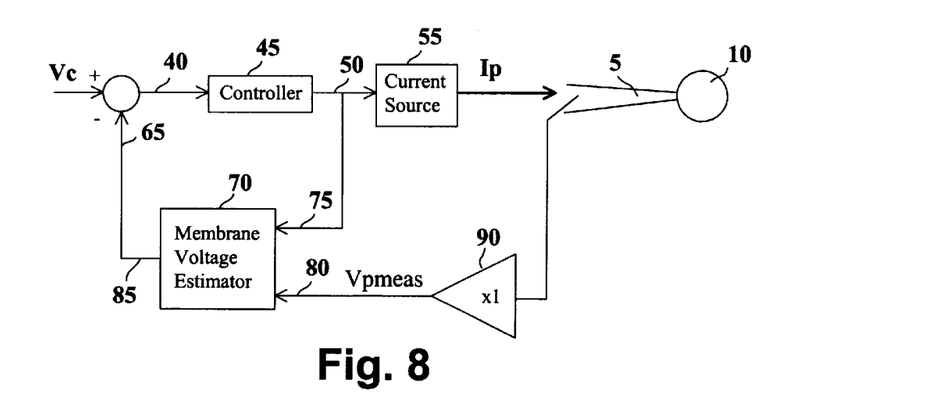
FIG. 8 shows the membrane voltage estimator being used to implement series resistance compensation in a single electrode voltage clamp

FIG. 8 illustrates this concept using the two electrode voltage clamp configuration previously shown in FIG. 4. In FIG. 4, the feedback signal 65 is formed by directly measuring the membrane voltage Vm using pipette 35 and buffer amplifier 60. Referring to FIG. 8, the feedback signal 65 is now formed by computing the membrane voltage Vm using the membrane voltage estimator 70. Control voltage 50 is used to form the Ipmeas 75 input signal to estimator 70, since control voltage 50 is a voltage proportional to the pipette current Ip, as required. This illustrates one embodiment of pipette current measurement means 74. To generate the other input signal needed by estimator 70, buffer amplifier 90 measures the pipette voltage Vp, thus forming input signal Vpmeas 80. Thus buffer amplifier 90 illustrates one embodiment of pipette voltage measurement means 79.

Using estimator 70 as outlined in FIG. 8 achieves 100% Rs compensation using a single electrode voltage clamp amplifier, achieving similar performance to a twin electrode voltage clamp amplifier. The voltage clamping bandwidth of FIG. 8 is greater than 10 kHz, enabling the study of rapid ionic current—such as $Na_+$ current in neurons and cardiac cells—to be readily resolved.

The large stability afforded by this method of compensation for series resistance is due to the absence of destabilizing pipette capacitance neutralization circuits, which plague conventional designs. Not only are such circuits themselves unstable, any residual capacitance due to imperfect neutralization seriously destabilizes conventional Rs compensation. The membrane voltage estimator, in contrast, simply uses the value of the pipette capacitance Cp as a parameter in its computation, and the resultant voltage clamp is not destabilized by the pipette capacitance Cp.

CONCLUSIONS, RAMIFICATIONS, AND SCOPE

The single electrode voltage clamp using the membrane voltage estimator of this invention enables the study of rapid ionic currents in single cells that could previously be studied only in large, multi-celled preparations using a twin electrode apparatus.

Compared with conventional single electrode amplifiers that achieve only partial Rs compensation before the onset of oscillations, this invention allows full (100%) Rs compensation with a significant increase in speed. Equally important, the invention brings this performance with large stability margins, making it easy to use. This stability translates to a much greater tolerance for parameter changes—such as changing bath fluid levels or drifting pipette series resistance—which greatly enhances its ease-of-use over conventional designs.

Although the description above contains many specificities, these should not be construed as limiting the scope of the invention but as merely providing illustrations of some presently preferred embodiments of this invention. Many other embodiments of the estimator are immediately apparent to one skilled in the art. For example, the entire estimator equation could be implemented digitally using a suitably fast digital signal processor and by sampling the Ipmeas and Vpmeas signals using an analog-to-digital converter. The derivation of the estimator equation E1 is based on modeling pipette 10 using a single RC section, as shown in Fig 1B. This derivation can immediately be generalized to a pipette more accurately modelled with numerous RC sections, at the expense of added complexity Thus the scope of the invention should be determined by the appended claims and their legal equivalents, rather then by the examples given.

I claim:

1. A machine for estimating a membrane voltage of a cell, said cell having a membrane resistance and a membrane capacitance, said machine comprising:

(a) a pipette electrode including a pipette current, a pipette voltage, a pipette series resistance, and a pipette shunt capacitance, and (b) a pipette current measurement means for generating a measured pipette current, and (c) a pipette voltage measurement means for generating a measured pipette voltage, and (d) an estimator means for computing a computed membrane voltage, wherein said estimator means uses said measured pipette current and said measured pipette voltage to compute said computed membrane voltage, and wherein said estimator means operates independently of said membrane resistance and said membrane capacitance, and wherein said estimator means operates without neutralizing said pipette shunt capacitance electronically.

2. The machine of claim 1, wherein said estimator means comprises:

(a) a voltage scaling means and differentiating means operating on said measured pipette voltage for generating a differentiated and scaled pipette voltage, and (b) a current scaling means operating on said measured pipette current for generating a scaled pipette current, (c) a summing means for generating a sum comprising said differentiated and scaled pipette voltage, said scaled pipette current, and said measured pipette voltage, and (d) a frequency equalizing means operating on said sum for increasing the bandwidth of said computed membrane voltage.

3. The machine of claim 1, wherein said estimator means comprises:

(a) a lowpass filter means and a scaling means operating on said measured pipette current for generating a lowpass filtered and scaled pipette current, and (b) a differencing means for generating a difference composed of said measured pipette voltage minus said lowpass filtered and scaled pipette current.

4. The machine of claim 3, wherein said estimator means includes a frequency equalizing means operating on said difference for increasing the bandwidth of said computed membrane voltage.

5. The machine of claim 1, wherein said computed membrane voltage is used in a feedback loop that forms a voltage clamp to maintain said membrane voltage at a command voltage, and wherein said pipette series resistance does not compromise the bandwidth of said voltage clamp.

6. A method for estimating a membrane voltage of a cell, said cell having a membrane resistance and a membrane capacitance, said method comprising:

(a) providing a pipette electrode including a pipette current, a pipette voltage, a pipette series resistance, and a pipette shunt capacitance, and (b) measuring a measured pipette current using a pipette current measurement means, and (c) measuring a measured pipette voltage using a pipette voltage measurement means, and (d) computing a computed membrane voltage using an estimator means, wherein said estimator means uses said measured pipette current and said measured pipette voltage, and wherein said estimator means operates independently of said membrane resistance and said membrane capacitance, and wherein said estimator means operates without neutralizing said pipette shunt capacitance electronically.

7. The method of claim 6, wherein said estimator means comprises:

(a) a voltage scaling means and differentiating means operating on said measured pipette voltage for generating a differentiated and scaled pipette voltage, and (b) a current scaling means operating on said measured pipette current for generating a scaled pipette current, (c) a summing means for generating a sum comprising said differentiated and scaled pipette voltage, said scaled pipette current, and said measured pipette voltage, and (d) a frequency equalizing means operating on said sum for increasing the bandwidth of said computed membrane voltage.

8. The method of claim 6, wherein said estimator means comprises:

(a) a lowpass filter means and a scaling means operating on said measured pipette current for generating a lowpass filtered and scaled pipette current, and (b) a differencing means for generating a difference composed of said measured pipette voltage minus said lowpass filtered and scaled pipette current.

9. The method of claim 8, wherein said estimator means includes a frequency equalizing means operating on said difference for increasing the bandwidth of said computed membrane voltage.

10. The method of claim 6, wherein said computed membrane voltage is used in a feedback loop to maintain said membrane voltage at a command voltage, forming a voltage clamp, wherein said pipette series resistance does not compromise the bandwidth of said voltage clamp.

11. A machine for estimating a membrane voltage of a cell, said cell having a membrane resistance and a membrane capacitance, said machine comprising:

(a) a pipette electrode including a pipette current, a pipette voltage, a pipette series resistance, and a pipette shunt capacitance, and (b) a pipette current measurement circuit to measure said pipette current, generating a measured pipette current, and (c) a pipette voltage measurement circuit to measure said pipette voltage, generating a measured pipette voltage, and (d) an estimator circuit, wherein said estimator circuit uses said measured pipette current and said measured pipette voltage to compute a computed membrane voltage, wherein said estimator circuit operates independently of said membrane resistance and said membrane capacitance, and wherein said estimator circuit operates without neutralizing said pipette shunt capacitance electronically.

12. The machine of claim 11, wherein said estimator circuit comprises:

(a) a voltage scaling means and differentiating means operating on said measured pipette voltage for generating a differentiated and scaled pipette voltage, and (b) a current scaling means operating on said measured pipette current for generating a scaled pipette current, (c) a summing means for generating a sum comprising said differentiated and scaled pipette voltage, said scaled pipette current, and said measured pipette voltage, and (d) a frequency equalizing means operating on said sum for increasing the bandwidth of said computed membrane voltage.

13. The machine of claim 11, wherein said estimator circuit comprises:

(a) a lowpass filter means and a scaling means operating on said measured pipette current for generating a lowpass filtered and scaled pipette current, and (b) a differencing means for generating a difference composed of said measured pipette voltage minus said lowpass filtered and scaled pipette current.

14. The machine of claim 13, wherein said estimator means includes a frequency equalizing means operating on said difference for increasing the bandwidth of said computed membrane voltage.

15. The machine of claim 11, wherein said computed membrane voltage is used in a feedback loop to maintain said membrane voltage at a command voltage, forming a voltage clamp, wherein said pipette series resistance does not compromise the bandwidth of said voltage clamp.

16. A method for estimating a membrane voltage of a cell, said cell having a membrane resistance and a membrane capacitance, said method comprising:

(a) providing a pipette electrode including a pipette current, a pipette voltage, a pipette series resistance, and a pipette shunt capacitance, and (b) measuring a measured pipette current using a pipette current measurement circuit, and (c) measuring a measured pipette voltage using a pipette voltage measurement circuit, and (d) computing a computed membrane voltage using an estimator circuit, wherein said estimator circuit uses said measured pipette current and said measured pipette voltage, and wherein said estimator circuit operates independently of said membrane resistance and said membrane capacitance, and wherein said estimator circuit operates without neutralizing said pipette shunt capacitance electronically.

17. The method of claim 16, wherein said estimator circuit comprises:

(a) a voltage scaling means and differentiating means operating on said measured pipette voltage for generating a differentiated and scaled pipette voltage, and (b) a current scaling means operating on said measured pipette current for generating a scaled pipette current, (c) a summing means for generating a sum comprising said differentiated and scaled pipette voltage, said scaled pipette current, and said measured pipette voltage, and (d) a frequency equalizing means operating on said sum for increasing the bandwidth of said computed membrane voltage.

18. The method of claim 16, wherein said estimator means comprises:

(a) a lowpass filter means and a scaling means operating on said measured pipette current for generating a lowpass filtered and scaled pipette current, and (b) a differencing means for generating a difference composed of said measured pipette voltage minus said lowpass filtered and scaled pipette current.

19. The method of claim 18, wherein said estimator means includes a frequency equalizing means operating on said difference for increasing the bandwidth of said computed membrane voltage.

20. The method of claim 16, wherein said computed membrane voltage is used in a feedback loop to maintain said membrane voltage at a command voltage, forming a voltage clamp, wherein said pipette series resistance does not compromise the bandwidth of said voltage clamp.

* * * * *